United States Patent [19]
McLauchlan

[11] Patent Number: 5,205,735
[45] Date of Patent: Apr. 27, 1993

[54] HEAD GEAR PILLOW

[76] Inventor: Staci B. McLauchlan, 1343 Delta Ave., Cincinnati, Ohio 45208

[21] Appl. No.: 835,769

[22] Filed: Feb. 14, 1992

[51] Int. Cl.⁵ .................................................. A61C 3/00
[52] U.S. Cl. ............................................ 433/5; 2/214
[58] Field of Search ...................... 433/5; 2/214, 215

[56] References Cited

U.S. PATENT DOCUMENTS

| | | | |
|---|---|---|---|
| 3,814,087 | 6/1974 | Heikes | 433/5 |
| 4,704,086 | 11/1987 | Armstrong et al. | 433/5 |
| 4,734,032 | 3/1988 | DeWoskin | 433/5 |
| 4,988,291 | 1/1991 | Grummons | 433/5 |

Primary Examiner—John J. Wilson
Attorney, Agent, or Firm—Dinsmore & Shohl

[57] ABSTRACT

One or more pads adapted to be secured between an orthodontic appliance and the cheeks. The pads have an interior side and exterior side, the exterior side having means to secure the pad to the orthodontic appliance.

2 Claims, 2 Drawing Sheets

HEAD GEAR PILLOW

1. BACKGROUND OF THE INVENTION

Orthodontic appliances have been developed which are worn by the patient for the purpose of having selected teeth moved or forced into a position relative to the mouth. Among the factors considered in designing such an appliance is patient comfort, especially when the patient is sleeping or lying prone. Typical orthodontic appliances have exposed metal, plastic and wires to the patient's face and cheeks which can cause discomfort as well as irritation for the patient. The discomfort and irritation may interrupt and interfere with the patient's ability to rest and sleep.

2. FIELD OF THE INVENTION

This invention relates to the field of orthodontic/facial appliances and more particularly to a new and improved pads adapted to protect the face and cheeks.

3. PRIOR ART

The present invention is used in connection with orthodontic appliances. U.S. Pat. No. 4,988,291 discloses an orthodontic appliance and method which includes a face crib which incorporates cheekbone elements attached to the appliance and bear against the cheekbone of the patient. The cheekbone elements comprise a padded metal support, but while the padding may offer the patient some improved comfort, the configuration disclosed really offers a hard surface to cheek. Armstrong, et al., U.S. Pat. No. 4,704,086, discloses an orthodontic appliance having a padded portion engaged with the side of the face adjacent to the margin of the mouth opening. Once again this device offers only a marginal improvement in patient comfort.

U.S. Pat. No. 3,203,099 issued to Interlandi uses sleeve members to cover a portion of an orthodontic appliance adjacent to cheekbones to protect the face. This too provides only a marginal increase in the patient's comfort.

Geiser, U.S. Pat. No. 4,682,374 and Davis, U.S. Pat. No. 3,006,274 discloses padded ear coverings and padded eyewear. None of these patents show the unique combination of the face pillows for an orthodontic appliance designed to provide comfort to the patient when at rest or sleep.

SUMMARY AND OBJECTIONS OF THE INVENTION

Accordingly, it is the primary object of this invention to provide a headgear pillow adapted for use with an orthodontic appliance.

It is a more particular object of this invention to provide pillows for use with an orthodontic appliance which protects the patient's face and in particular the patient's cheeks.

It is an additional object of this invention to provide pillows which may be easily secured to and easily removed from the orthodontic appliance and which may be cleaned and replaced.

It is a further object of this invention to provide a soft and cushioned surface to the patient's face.

Yet another object of this invention is to provide pads for an orthodontic appliance which offers the patient increased comfort when sleeping or lying prone.

In accordance with the invention, an orthodontic appliance is adapted to be worn during the night or other periods of rest. The orthodontic device is adapted by the use of a combination of head gear pillows which provide protection for the patient's face. Two round pillows are fitted to the side and front of the appliance to provide cushioning for the cheeks. The cheek pillows have an interior side which protects the patient's cheeks and an exterior side which has a means for securing the pillow to the orthodontic appliance. An elongated pillow may be fitted to the back of the device to provide cushioning for the neck.

The above will become more apparent to those skilled in the art after a consideration of the following detailed description taken together with the accompanying drawings in which a preferred embodiment of the invention is described.

DETAILED DESCRIPTION OF THE PREFERRED EMBODIMENT

Figure 1:
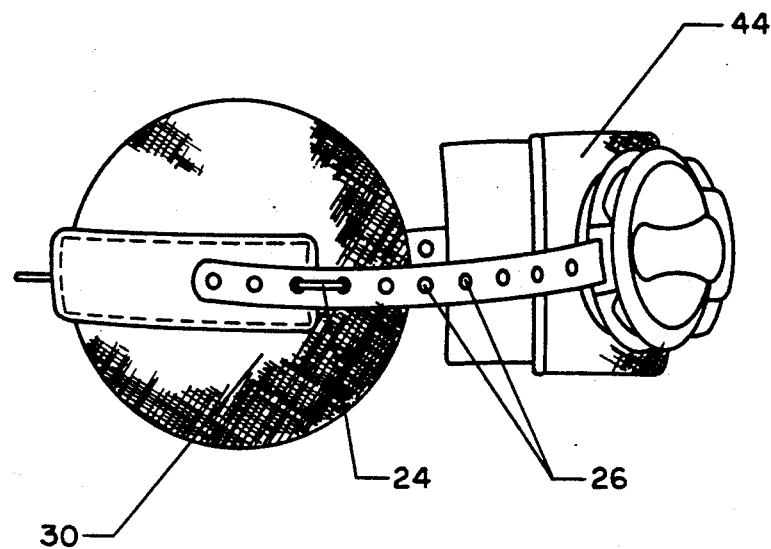
FIG. 1 is a side elevational view of an orthodontic appliance fitted with the headgear pillows.
Figure 2:
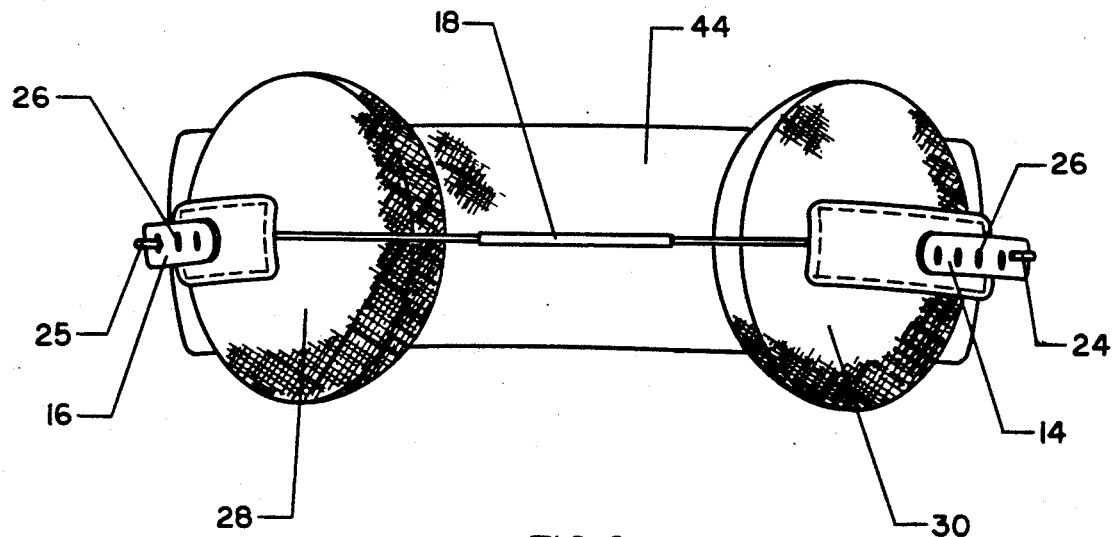
FIG. 2 is a frontal elevational view of an orthodontic appliance fitted with the headgear pillows.
Figure 3:
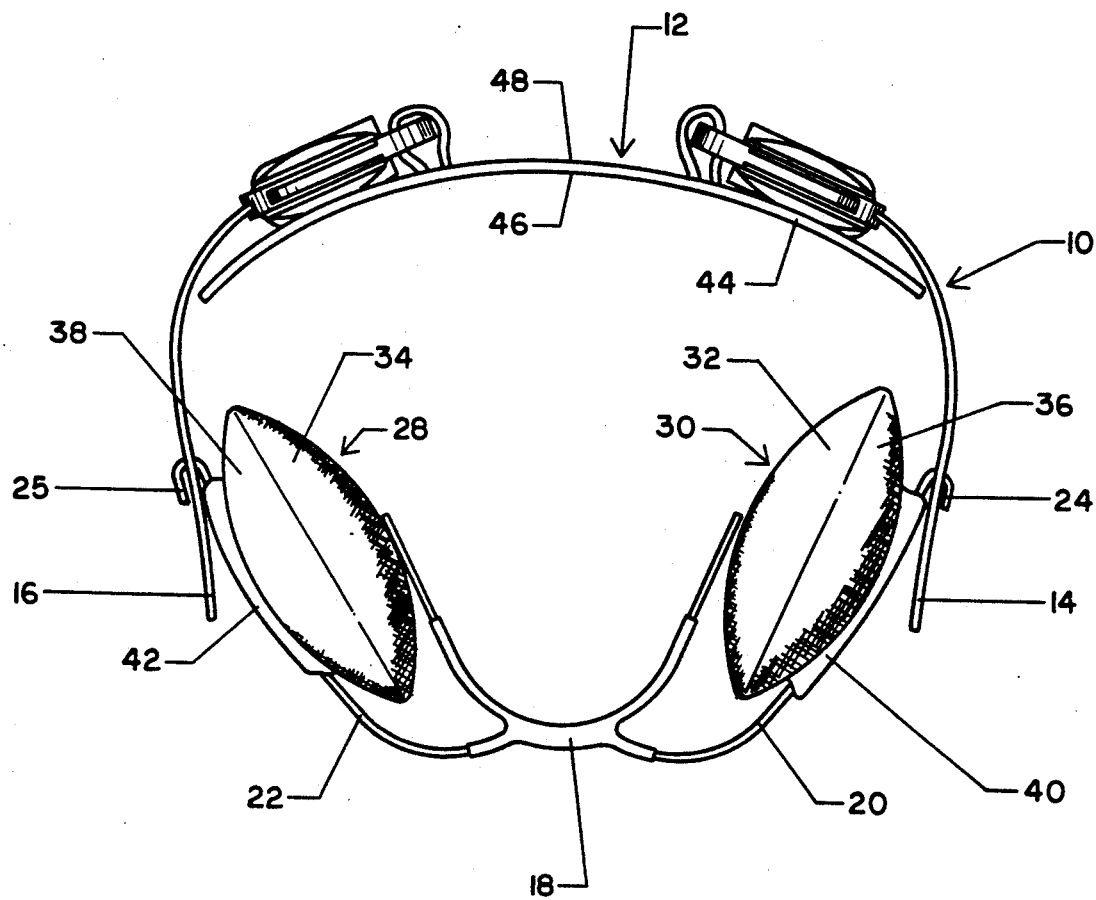
FIG. 3 is a top plan view of the headgear pillows fitted to the orthodontic appliance.

The head gear pillow of the present invention comprises a pair of approximately round pillows adapted to fit on the side and front of an orthodontic device. An elongated rectangular pillow is adapted to fit in the rear of the orthodontic device. These pillows protect the patient's face from the metal wire and hard plastic parts of the orthodontic device. The present invention permits the patient to rest comfortably and sleep without interruption. The pillows are designed to easily attach to the orthodontic device. Similarly, the pillows may be quickly and easily removed for washing and then replaced on the orthodontic device. The pillows are primarily intended for use with "Cervical-Pull" headgears but may also be used with "Straight-Pull" and "Combi" headgears.

Referring now to the drawings, the orthodontic device comprises a curved rear piece (12), a pair of side pieces (14, 16) and a mouth bow (18). The sides (20, 22) of the mouth bow (18) are curved to form hooks (24, 25) to engage one of a series of adjustable holes (26) of the side pieces (14, 16).

A pair of pillows (28, 30) approximately round in shape are designed to fit on the sides (20, 22) of the mouth bow (18). When the hooks of the mouth bow (18) have been disengaged from the openings (26) of the side pieces (14, 16). The face pillows (28, 30) are made of a pillow casing which is a suitable material such as cotton flannel to provide softness when in contact with the face. It is preferred to use 100% colorfast cotton flannel treated with a non-toxic retardant. Preferably washable material is used for the casing. The face pillows are stuffed with a suitable cushioning material such as quilt batting to provide softness and cushioning. The face pillows are fitted to the space between the cheek and accordingly prevent the mouth bow (18) from coming into contact with the face.

The face pillows (28, 30) have an interior side (32, 34) and an exterior side (36, 38). The interior side is designed to contact the patient's cheek and the exterior side is designed with a strap (40, 42) to receive the side (20, 22) of the mouth bow (18). Other means maybe used to secure the pillow in a position between the side (20, 22) of the mouth bow (18) and the patient's cheek such as velcro strips as long as the pillows remain in position between the cheek and the mouth bow. The unique design of the strap permits quick and easy placement of the pillows on the orthodontic device. Further, the design is adapted for simple removal of the pillows for washing.

A typical cheek pillow is approximately two and one-half inches in diameter and approximately seven and seven-eights inches in circumference. At the center of the pillow the width is approximately seven-eighths to an inch in thickness. The width tapers to the outside of the pillow.

The strap (40, 42) is approximately two inches by five-eights inches and is attached to the center of the exterior side of the pillow and typically stitched lengthwise to the casing. The strap is usually the length of the pillow that is approximately two inches. The ends of the strap are not stitched to the casing and thus allow approximately seven sixteenths of an inch for passage of the side bar between the strap and the pillow.

The rear of the orthodontic appliance may be fitted with a elongated curved pillow (44) which protects the neck from contact with the rear piece (12) of the device. The neck pillow may be made of similar fabric and stuffing as the face pillows. The neck pillow (44) has an interior side (46) and an exterior side (48). The interior side is in contact with and cushions the patient's neck and prohibits contact between the rear piece (12) and the patient's neck. This neck pillow in combination with the face pillows have significant advantages when the patient is supine and offers a measure of comfort heretofore missing in orthodontic devices.

It will be understood that the foregoing description and illustrations is by way of example only and such modifications and changes as may suggest themselves to those skilled in the art are intended to fall within the scope of the present invention as defined by the claims.

I claim:

1. A head gear pillow for use with an orthodontic appliance comprising
   a pair of face pillows adapted to fit on sides of said orthodontic appliance;
   said face pillows having an interior side and an exterior side; said exterior side of said face pillows having means to secure said face pillow on sides of a mouth bow;
   wherein said face pillows have a diameter of approximately 2.5 inches and a width of 162 to one inch.

2. A head gear pillow according to claim 1 wherein said means to secure said face pillows to said sides of said mouth bow is a strap centered on said exterior of said face pillows.

* * * * *